United States Patent [19]

Pelling

[11] Patent Number: 5,314,419
[45] Date of Patent: May 24, 1994

[54] METHOD FOR DISPENSING OPHTHALMIC DRUGS TO THE EYE

[76] Inventor: George E. Pelling, 9441 Mokihana Dr., Huntington Beach, Calif. 92646

[21] Appl. No.: 968,992

[22] Filed: Oct. 30, 1992

[51] Int. Cl.⁵ ............................................ A61M 35/00
[52] U.S. Cl. ................................... 604/294; 604/295; 604/290; 604/892.1
[58] Field of Search ............... 604/289, 290, 294, 295, 604/298, 300, 892.1, 8

[56] References Cited

U.S. PATENT DOCUMENTS

| | | | |
|---|---|---|---|
| Re. 28,873 | 6/1976 | Morgan | 128/249 |
| 772,028 | 10/1904 | Carpenter . | |
| 3,392,725 | 7/1968 | Behney | 128/249 |
| 3,626,940 | 12/1971 | Zaffaroni | 604/294 |
| 3,630,200 | 12/1971 | Higuchi et al. | 128/260 |
| 3,818,909 | 6/1974 | Bratton | 128/232 |
| 3,916,899 | 11/1975 | Theeuwes et al. | 604/294 |
| 3,995,635 | 12/1976 | Higuchi et al. | 128/260 |
| 4,014,334 | 3/1977 | Theeuwes et al. | 604/294 |
| 4,036,230 | 7/1977 | Adams | 604/294 |
| 4,052,505 | 10/1977 | Higuchi et al. | 424/14 |
| 4,111,200 | 5/1978 | Sbarra et al. | 128/233 |
| 4,117,842 | 10/1978 | Hutchins | 128/163 |
| 4,540,408 | 9/1985 | Lloyd | 604/290 |
| 4,733,802 | 3/1988 | Sheldon | 222/181 |
| 4,838,851 | 6/1989 | Shabo | 604/294 |

OTHER PUBLICATIONS

Vincent H. L. Lee, New Directions In the Optimization of Ocular Drug Delivery, vol. 6, No. 2, (1990), pp. 157-164.

Primary Examiner—Paul Prebilic
Attorney, Agent, or Firm—John F. Sicotte

[57] ABSTRACT

An ophthalmic drug dispensing system in the form of a hand held device constructed of a soft pliable material with a bleb or bulbous area in its forward portion. Contained within the bleb is a fluid chamber which is connected to an orifice located in one end of the dispensing system.

In use, the chamber is filed with a drug or medication and the device is inserted between the sclera of the eye and the upper eyelid with the bleb contacting the inner surface of the eyelid. Due to the pressure of the inner side of the upper eyelid upon the bleb, the drug or medication is forced from the chamber and out through the orifice by way of the channel.

2 Claims, 2 Drawing Sheets

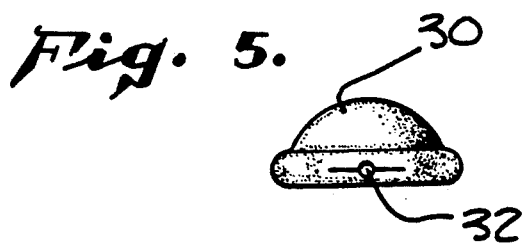
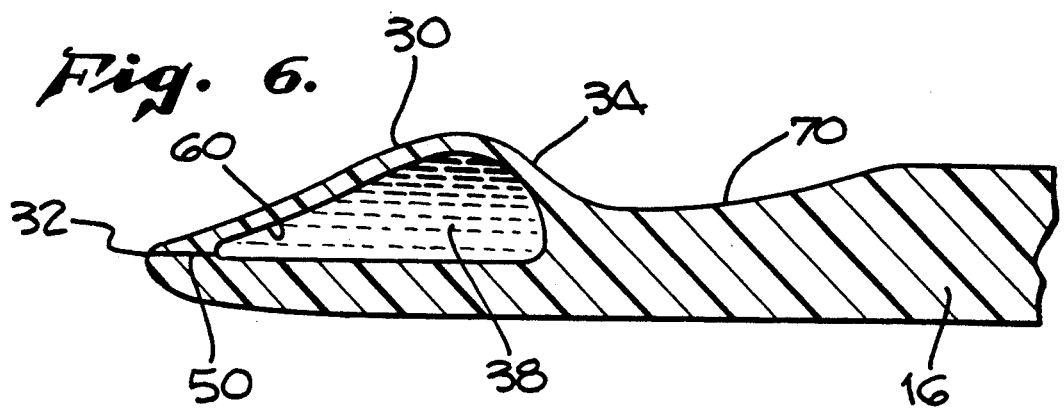
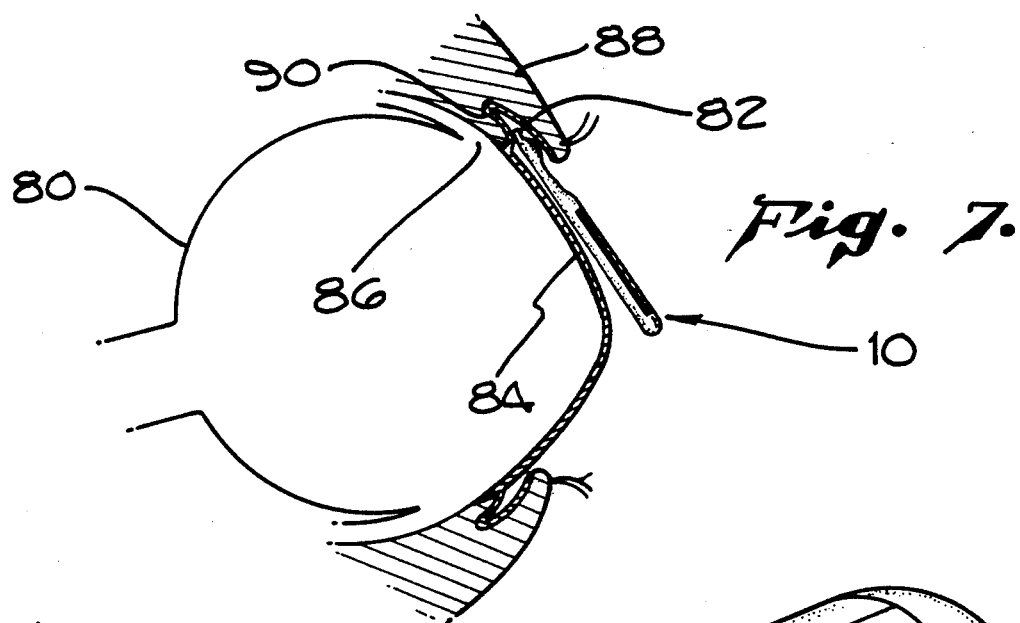
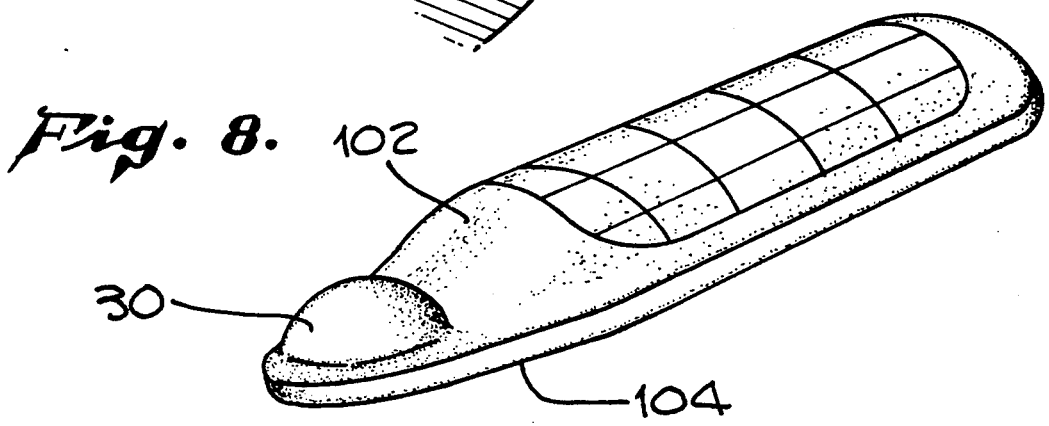

METHOD FOR DISPENSING OPHTHALMIC DRUGS TO THE EYE

BACKGROUND OF THE INVENTION

It is commonplace in the field of ophthalmology to topically apply medication a patient's eye by applying a fluid onto the surface of the cornea of the eye. Due to the ease of administration; eye drops are administered to the lower fornix, the potential space between the eye and the lower lid. Recent research has indicated more used efficiency with eye drops placed into the upper fornix, the potential space between the eye and the upper lid, using conventional eye drop dispensers in order to apply drops under the upper lid, the patent will be placed in a supine position or will need to put his/her head back while facing the ceiling. For some patients this can be a problem due to physical infirmities, the lack of a bed to lie on, hand tremor and the difficulties with hand eye coordination. Another problem with the usual method of applying topical medicine is the use of preservatives which may irritate the eye and cause tearing with subsequent decrease in efficiency of the medication due to "washout."

In addition to the application problems traditionally associated with the use of eye droppers is the amount of medication needed to achieve a certain result. Studies have shown that if eye medication is applied beneath the superior fornix of a patient, the medication will have an increased absorption rate and increased duration. A recent article discussing this issue was published in the Journal of Ocular Pharmacology, by Vincent H. L. Lee, dated May 25, 1990. According to Dr. Lee, for the last twenty years the main effort has been to design systems to prolong the residence time of topically applied drugs in the conjunctival sac. The approach has been to minimize precorneal drug loss through prolongation of residence time of the drug in the conjunctival sac. The major route by which most ophthalmic drugs enter the eye is traditionally believed to be via the cornea. There is increasing evidence which shows that topically applied ophthalmic drugs can reach the posterior of the eye by diffusion across the conjunctiva-sclera laminate. This route is favored because there are drugs which are poorly absorbed by the cornea compared to a more posterior route, such as some anti-glaucoma medication. Micro-particulate systems, such as nanoparticles and microspheres, may favor non-corneal drug penetration since they may accumulate in the fornices. The present invention provides an ophthalmic drug delivery system specifically designed to promote non corneal drug penetration. As well as a prolonged and more effective method of corneal absorption through the upper fornix, lid administration.

For many patients an improved drug delivery system for ophthalmic drugs may be of critical importance. Medication which is absorbed through the eye will commingle with other medicines present in a patient's system. The combination of certain types and levels of medication can be problematic for the patient. However, this problem can be lessened by using eye medications which are applied in doses which are efficacious yet smaller than the amount which is used with current eye droppers.

Another problem with the use of eye droppers is sterility. When a dropper is used and then replaced back in its container, there is a chance that the medication could become contaminated. Currently applied medications require the use of a preservative in order to maintain their safe use and effectiveness including medicines that are designed for use in ocular insert devices. This is problematic since some patients have an allergic reaction or chemical reaction to the preservative contained in the medicine. This type of allergic reaction causes "washing out" of the medication due to the severe tearing of the eye.

Another problem with medications which are supplied in drop form or in a continuous use device, is the occurrence of side effects. Depending upon the makeup of a particular patient, some types of medication can cause psychosis, heart problems and even a accidental heart attack due to systemic side effects. Lower lid application of medications may be absorbed systematically especially after entering the nasal mucosa.

PRIOR ART

Prior art includes U.S. Pat. No. 3,630,200 issued Dec. 28, 1971, entitled OCULAR INSERT (the "ALZA '71 Patent"); U.S. Pat. No. 3,995,635 issued Dec. 7, 1976, entitled OCULAR INSERT (the "ALZA '76 Patent"); and U.S. Pat. No. 4,052,505 issued Oct. 4, 1977, entitled OCULAR THERAPEUTIC SYSTEM MANUFACTURED FROM COPOLYMER (the "ALZA '77 Patent").

The Alza '71 Patent claims an ocular insert for dispensing drugs which is constructed of a soft hydrophilic outer layer and a porous inner core which stores and dispenses liquids continuously over a prolonged period of time. The device is inserted into the cul-de-sac of the conjunctiva between the sclera of the eyeball and the eyelid.

The device disclosed in the Alza '76 Patent is another ocular insert containing a drug and is designed to dispense drugs over a prolonged period. It has an annular shape and is fitted into the cul-de-sac of the conjunctiva between the sclera of the eye and the upper eyelid. Additionally, it contains a conjoint detent means which operates to facilitate insertion of the device into the upper and lower conjunctiva sacs.

The Alza '77 Patent shows a device for releasing a drug at a continuous and controlled rate for a prolonged period of time. It is constructed of a polymeric material which contains a drug which permeates through the polymeric material by diffusion.

SUMMARY OF THE INVENTION

The present invention provides a ophthalmic drug delivery system for applying topical ocular medication to the upper fornix area of the eye. The device releases the medication when the patient or the treating person first places the device between the upper eyelid and the eye and then removes the device from under the upper lid. The pressure of the upper lid presses downward on the rear of a bleb, causing it to release the medication through an orifice located at a forward location on the bleb, thereby storing the ocular medication within the fornix for prolonged efficiency.

According to one particular feature of the invention, the orifice can be located anywhere on the bleb. For example, the orifice can be located in the leading surface of the bleb for dispensing fluids in a direction toward the back of the eye. The orifice can also be located at the upper most point on the bleb in order to deliver the medication toward the inner surface of the upper eyelid.

According to another feature of the present invention is that the upper layer with the bleb may be made of a substance which is more rigid and durable relative to the material that comprises the lower layer. This allows for a device which is easier to handle and place under the upper lid, yet has a lower surface that is comfortable to the eye.

In accordance with another feature of the invention the leading edge of the forward portion of the device can be shaped to accommodate needs of the patient. It can be made very wide or narrow. It also can be made to taper to a very thin edge.

In the preferred embodiment of the invention the shape of the bulbous area or bleb is generally oval. In an alternative form, the bleb can be made more rectilinear, square or triangular. Also, the height of the bleb may be varied to accommodate more or less fluid.

Thus, one object and purpose of the invention is to provide an ophthalmic drug delivery system designed to minimize loss medication by prolonging the residence time in the conjunctival sac, particularly within the upper fornix.

Another object of the present invention is to promote noncorneal drug penetration by periodic applications of medication to the upper fornix region, thereby expanding the exposed surface area to include not only the anterior segment but the posterior segment as well.

Another object of the invention is to provide a precorneal ophthalmic drug delivery system which can periodically supply medication in single pre-measured doses and which medication does not contain any preservatives since it can be packaged in a sterile system.

Another object of the invention is to provide a drug delivery system which is more effective and efficient resulting in the need for smaller doses with lower cost and diminished system's side effects.

Another object and purpose of the invention is to provide a drug delivery system that uses non corneal absorption through the upper fornix which allow for more direct medication of the posterior and superior areas of the eye.

Another object of the present invention is to provide an extended duration of corneal application of medication or fluids. This will promote increased absorption of medication into the cornea and anterior segment of the eye. It will also extend the duration of action of such medications as ocular lubricants, hyper-osmotic agents for the cornea, etc.

Thus, one object and purpose of the invention is to provide a ophthalmic fluid or medicine dispensing device that is easier to handle by the patient or other persons applying eye medication in the form of fluids.

DRAWING SUMMARY

FIG. 5 is front elevational view of the invention showing the fluid channel in open position.

FIG. 6 is a cross section elevational view of the invention taken along A—A' in FIG. 3.

FIG. 7 is a side elevational view of the invention in dispensing position under the upper eyelid.

FIG. 8 is a prospective view showing the alternative embodiment of the invention.

DETAILED DESCRIPTION

Figure 1:
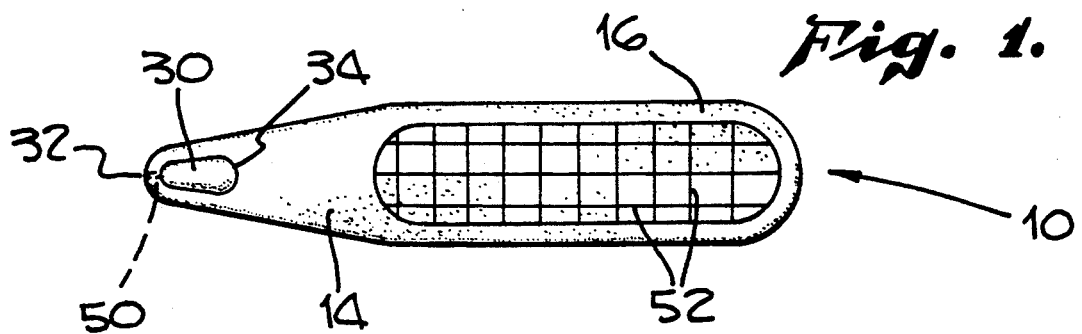
FIG. 1 is a top view of the invention.

Referring now to the drawings, FIG. 1 shows a top view an ophthalmic drug dispensing device 10 having a forward portion 14 and a rearward portion 16. In forward portion 14 there is a bulbous area or bleb 30. As indicated in FIG. 1, bleb 30 is connected with orifice 32 by way of channel 50. Bleb 30 also has a sloped area 34 located at its rear edge.

Figure 2:
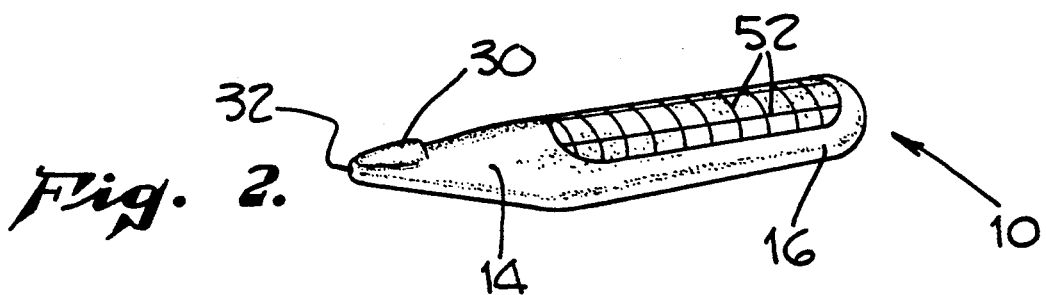
FIG. 2 is a perspective view showing the invention in its preferred embodiment.

FIG. 2 shows a perspective view of the ophthalmic device shown in FIG. 1. This is the preferred embodiment of the invention with a generally round or oval shaped bleb 30 which contains an orifice 32 located in its forward surface. FIG. 2 also shows that rearward portion 16 has a texturized top surface 52 to facilitate handling.

Figure 3:
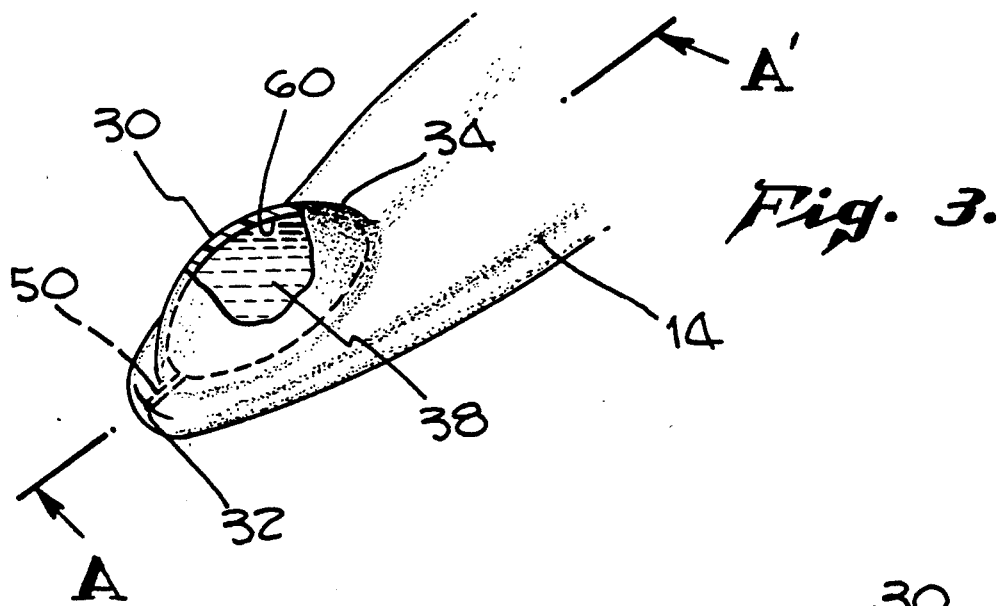
FIG. 3 is a perspective view of the front portion of the invention.

FIG. 3 shows a perspective view of forward portion 14 of the preferred embodiment. As can be seen in FIG. 3, fluid 38, which can be a medicine, is located within bleb 30. Within the forward surface of 30 is orifice 32 which is connected by way of channel 50 to chamber 60 formed within bleb 30. When sufficient pressure is applied to bleb 30 at its rear surface 34, the fluid will be released through channel 50 and out orifice 32.

Figure 4:
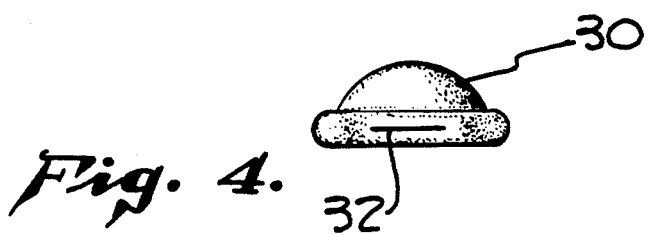
FIG. 4 is a front elevational view showing the invention with the fluid channel in closed position.

FIG. 4 shows a front elevational view of the invention. It should be noted that only the exterior end of orifice 32, which in this view, is shown in its naturally closed position.

FIG. 5 shows the same end view with orifice 32 in open position, as if it were dispensing a fluid.

The preferred embodiment of the invention is shown in FIG. 6. This is a cross-sectional view which shows that bleb 30 may take many shapes depending upon the needs of the patient. In this embodiment the bleb has a generally rounded rear surface 34 to provide a larger surface area for which the upper eyelid to press against. Also, rearward portion 16 has a reduced cross-sectional area at 70 to provide a surface area for an upper eyelid to press upon. This will increase the pressure inside chamber 60. When the invention is withdrawn from under the upper eyelid, fluid 38 will be dispensed through channel 50 and out of the dispenser at orifice 32.

Reference is now made to FIG. 7 which is a cross-sectional side elevational view of a human eye 80. The invention 10 is shown in the cul-de-sac 82 of the conjunctiva 84 between the sclera 86 of the eyeball and the upper eyelid 88. When the fluid is dispensed, upon retraction of the invention from under the eyelid 88, the fluid will be deposited in a precise amount into the fornix of the upper lid.

A method of administering a fluid medication or drug to the upper fornix area of a patient's eye with the device involves selecting a medication or drug to be administered, filling the chamber with the drug of medication, and inserting the forward end of the device and bleb under the upper eyelid so the orifice is directed toward the cul-de-sac. Next, the upper eyelid is allowed to rest upon the bleb. Then, the device is withdrawn so that the pressure of the upper eyelid over the bleb presses downward on the bleb such that the drug of fluid medication will be dispensed through the channel, out the orifice, and into the upper fornix area.

ALTERNATIVE EMBODIMENT

The invention has been illustrated in its presently preferred form such that the ophthalmic drug dispenser is a simple unit construction which is composed of one type of material. However, it is also possible to construct the invention in such a manner that it has an upper layer and a lower layer. This alternative embodiment is illustrated in FIG. 8. Upper layer 102 can be composed of a type of synthetic material which is adaptable to forming bleb 30 and texturized top surface 52. Lower layer 104 may be constructed from a material that is more comfortable when it is touching the surface of the eye.

That which is claimed is:

1. A method for administering a drug to the upper fornix area of a patient's eye so as to allow for direct medication of the posterior and superior of the eye; the method comprising the steps of:
   selecting a hand held dispensing device including a body with a forward end, a top surface, said body containing a chamber, a channel connecting the chamber with an orifice located in the forward end of the body, and a bleb located on the top surface over the chamber;
   selecting a drug to be administered;
   filling the chamber with the drug;
   inserting the forward end of the device under the upper eyelid so that the orifice of the device is directed toward the cul-de-sac and advancing it to a point where the bleb is under the upper eyelid;
   allowing the upper eyelid to rest upon the top surface of the device and bleb;
   then withdrawing the device from under the upper eyelid so that the pressure of the upper eyelid presses downward on the bleb so that the drug will be dispensed through the channel, out of the orifice, and into the upper fornix.

2. A method for administering a fluid medicine to the cul-de-sac of the conjunctiva area of a patient's eye so as to allow for direct medication of the posterior and superior areas of the eye; the method comprising the steps of:
   selecting a hand held dispensing device including a body with a forward end, a top surface, said body containing a chamber, a channel connecting the chamber with an orifice located in the forward end of the body, and a bleb located on the top surface over the chamber;
   selecting a fluid medicine to be administered;
   filling the chamber by way of the orifice and channel with the fluid medicine;
   inserting the forward end of the device under the upper eyelid so that the orifice of the device is directed toward the cul-de-sac and advancing it to a point where the bleb is under the upper eyelid;
   allowing the upper eyelid to rest upon the top surface of the device and bleb;
   then withdrawing the device from under the upper eyelid so that the pressure of the upper eyelid presses downward on the bleb so that the drug will be dispensed through the channel, out to the orifice, and into the cul-de-sac.

* * * * *